(12) United States Patent
Ebnet

(10) Patent No.: US 11,744,611 B2
(45) Date of Patent: Sep. 5, 2023

(54) PUNCTURE SYSTEM

(71) Applicant: EBNET MEDICAL GMBH, Schwerin (DE)

(72) Inventor: Jens Ebnet, Schwerin (DE)

( * ) Notice: Subject to any disclaimer, the term of this patent is extended or adjusted under 35 U.S.C. 154(b) by 567 days.

(21) Appl. No.: 16/966,546

(22) PCT Filed: Jan. 24, 2019

(86) PCT No.: PCT/EP2019/051751
§ 371 (c)(1),
(2) Date: Jul. 31, 2020

(87) PCT Pub. No.: WO2019/149615
PCT Pub. Date: Aug. 8, 2019

(65) Prior Publication Data
US 2022/0175416 A1 Jun. 9, 2022

(30) Foreign Application Priority Data
Feb. 2, 2018 (DE) ...................... 10 2018 102 390.1

(51) Int. Cl.
*A61B 17/34* (2006.01)
*A61M 29/02* (2006.01)

(52) U.S. Cl.
CPC .. *A61B 17/3415* (2013.01); *A61B 2017/3492* (2013.01); *A61M 29/02* (2013.01)

(58) Field of Classification Search
CPC ....... A61B 17/3415; A61B 2017/3492; A61M 29/02; A61M 2025/0006;
(Continued)

(56) References Cited

U.S. PATENT DOCUMENTS 4,763,667 A 8/1988 Manzo
6,283,958 B1 * 9/2001 Vogl ..................... A61N 5/0601
606/7
(Continued)

FOREIGN PATENT DOCUMENTS

DE 10215191 A1 10/2003
EP 2 662 107 A2 11/2013
(Continued)

*Primary Examiner* — Amber R Stiles
*Assistant Examiner* — Nelson Louis Alvarado, Jr.
(74) *Attorney, Agent, or Firm* — WCF IP

(57) ABSTRACT

The invention relates to a puncture system having an outer tubular body which is designed to remain in a body part of a living being, said puncture system comprising at least one inner tubular body and a puncture needle, wherein the inner tubular body is guided through a working lumen of the outer tubular body and is longitudinally displaceable relative to the outer tubular body, and the puncture needle is guided through a puncture lumen of the inner tubular body and the inner tubular body is longitudinally displaceable relative to the puncture needle. The puncture system has a manually actuatable element that can be moved by manual actuation at least into a fixing position and into a release position, wherein, in the fixing position, the longitudinal displaceability a1) of the inner tubular body relative to the outer tubular body and/or a2) of the puncture needle relative to the inner tubular body and/or a3) of the puncture needle relative to the outer tubular body is removed or reduced.

14 Claims, 5 Drawing Sheets

(58) Field of Classification Search
CPC ...... A61M 2025/0175; A61M 25/0606; A61M 25/065; A61M 25/0662; A61M 2205/0238
See application file for complete search history.

(56) References Cited

U.S. PATENT DOCUMENTS

| | | | | |
|---|---|---|---|---|
| 6,419,643 | B1* | 7/2002 | Shimada | A61M 25/00 |
| | | | | 600/585 |
| 2004/0147877 | A1* | 7/2004 | Heuser | A61M 25/0662 |
| | | | | 604/165.02 |

FOREIGN PATENT DOCUMENTS

| | | | |
|---|---|---|---|
| WO | 1999/037354 | A1 | 7/1999 |
| WO | 2003/077982 | A2 | 9/2003 |
| WO | 2008/092029 | A2 | 7/2008 |
| WO | 2012/162677 | A1 | 11/2012 |
| WO | 2017/017095 | A1 | 2/2017 |

* cited by examiner

PUNCTURE SYSTEM

The invention relates to a puncture system having an outer tubular body which is designed to remain in a body part of a living being, wherein the puncture system has at least one inner tubular body and a puncture needle, wherein the inner tubular body is guided through a work lumen of the outer tubular body and is longitudinally displaceable relative to the outer tubular body, and the puncture needle is guided through a puncture lumen of the inner tubular body, and the inner tubular body is longitudinally displaceable relative to the puncture needle.

WO 2017/017095 A1 describes a puncture system, said puncture system being composed of three elements that are guided in a displaceable manner relative to one another.

Such puncture systems can be used, for example, as a central venous catheter, wherein the outer tubular body can be configured as a catheter hose. The latter is inserted into the body via a punctured peripheral vein, and its tip is positioned in a central vein near the heart. Liquids, medicaments or chemotherapy agents, for example, can be injected via a central venous catheter. Central venous catheters are designed to be able to remain in the patient even for weeks at a time. The inner tubular body replaces the Seldinger wire that is used in the standard placement of a central venous catheter. The inner tubular body is introduced into the punctured vein as a guide body for the catheter hose, such that the catheter hose then only has to be advanced over the inner tubular body until it is in the correct position. The puncture system is thus constructed of three layers.

The object of the invention is therefore to further develop such a puncture system.

The object is achieved with a puncture system having the features of claim 1, and with a tubular body having the features of claim 16. Advantageous embodiments are described in the dependent claims.

It is proposed that the puncture system has a manually actuatable fixing element which can be moved by manual actuation at least into a fixing position and into a release position, wherein, in the fixing position, the longitudinal displaceability
  of the inner tubular body relative to the outer tubular body
    and/or
  of the puncture needle relative to the inner tubular body
    and/or
  of the puncture needle relative to the outer tubular body
  is canceled or reduced.

The invention has the advantage that a user can apply the puncture system to the patient more easily and more safely than in known solutions. Here, the fixing element serves to fix the different layers of the puncture system relative to one another, wherein the longitudinal displaceability of the individual layers is thereby reduced or canceled. In this way, undesired movements of the puncture needle, of the inner tubular body and/or of the outer tubular body are avoided. It is thus conceivable, for example, that the longitudinal displaceability of the inner tubular body relative to the outer tubular body is reduced or canceled. This avoids a situation in which, when a living being is punctured by the puncture needle, undesired movements of the inner tubular body and outer tubular body in the direction of the punctured body part take place. However, it is also possible that the puncture needle can be moved into a fixing position relative to the inner tubular body such that, after the puncture has been performed and the inner tubular body has been inserted into the punctured body part, a movement of these elements is avoided. It is moreover possible to fix the puncture needle relative to the outer tubular body, thereby ensuring safe guiding of the inner tubular body into the punctured body part. It is also conceivable that the puncture needle, the inner tubular body and the outer tubular body can be moved into a fixing position relative to one another, e.g. in order to secure the puncture system against undesired lengthwise movements of the individual layers after the puncture system has been applied to a patient. The different fixing positions of the puncture system can be made discernible to the user by touch, e.g. by corresponding markings on the puncture system.

Alternatively, or in combination with this solution, the puncture system can have a sealing element by which the inner tubular body is sealed off relative to the outer tubular body at least at the end near the patient. Such sealing ensures that no exchange of fluids can take place between the inner tubular body and the outer tubular body. Thus, undesired suction of air can also be avoided during aspiration.

Alternatively, or in combination with the preceding solutions, the puncture system can have, at the end near the patient, a dilation body which serves for inserting the outer tubular body into the body part and through which the inner tubular body is guided, wherein the dilation body tapers at an acute angle of less than 11 degrees, proceeding from a 360° system. The angle relates to the angular extent between two outer dilation surfaces of the dilation body and not to the central axis of the dilation body.

Advantageously, the dilation body can taper at an acute angle of less than 10.5 degrees. This has the advantage that the outer tubular body can be inserted into the punctured body part easily and without additional widening of the puncture site, by means of the dilation body being pushed over the inner tubular body into the punctured body part, in which process the required dilation takes place and the outer tubular body can be pushed into the body part. For this purpose, it is necessary that the dilation body tapers at an acute angle of less than 11 degrees, in particular less than 10.5 degrees, such that it can advance through the skin in the dilation process. It is conceivable that the dilation body is made of a material, or is coated with a material, that reduces the frictional resistance, so as to facilitate an advance of the dilation body. It is also conceivable that, after the dilation body has been inserted into the punctured body part, it is widened and therefore widens the puncture site, such that the outer tubular body can be pushed into the punctured body part.

According to an advantageous development, it is possible that, in the fixing position, the longitudinal displaceability can be reduced, by means of the fixing element, to an extent that can be set by the manual actuation. Advantageously, the fixing element can be moved, by manual actuation, into different fixing positions in which the longitudinal displaceability can be reduced to respectively different extents. This has the advantage that the longitudinal displaceability can be reduced by the user to different extents depending on the particular requirements. It is thus possible, for example, to cancel the longitudinal displaceability or only to reduce it by a certain extent, that is to say to increase the resistance of the individual layers relative to one another, if this is deemed necessary by the user. Advantageously, the fixing element can be moved, by manual actuation, into different fixing positions in which the longitudinal displaceability is adjustable in terms of
  the inner tubular body relative to the outer tubular body
    and/or
  the puncture needle relative to the inner tubular body
    and/or the puncture needle relative to the outer tubular body.

In an advantageous embodiment, the fixing element of the puncture system can be designed as a clamping element or can have a clamping element, wherein by means of the clamping element the inner tubular body can be clamped relative to the outer tubular body and/or the puncture needle can be clamped relative to the inner tubular body and/or the puncture needle can be clamped relative to the outer tubular body.

By the provision of a clamping element, the individual layers of the puncture system can be partially or completely fixed relative to one another, so as to be able to ensure a secure position of the puncture system. The clamping element can be designed here in the manner of a collet chuck with a conically slotted sleeve and a union nut, wherein, by tightening of the union nut, the individual layers are pressed into the inner cone of the sleeve and thus clamped. However, the following alternatives are also conceivable:

An expansion body which is introduced into the puncture system in order to fix the individual layers, wherein expansion of the expansion body has the effect that the inner layers are pressed against the outer layers and thus fixed.

A clip system, wherein the individual layers are fixed against one another by pressure when a clip located outside the puncture system is folded back.

A screw which is introduced into the puncture system through a corresponding bore, wherein turning of the screw fixes the individual layers against one another with pressure.

A coating of the individual layers of the puncture system can be designed such that the longitudinal displaceability is limited by comparison with the conventional system.

It is also possible that the individual layers can latch into one another, e.g. by means of notches.

The individual layers can be wedged in one another by means of having a non-circular diameter or, at individual locations, an increased diameter, and they are therefore at least partially fixed relative to one another during rotation or during advance and retraction of the individual layers.

The clamping element can be designed such that, in a position in which it is not contacted e.g. by a spring mechanism, it fixes all the layers relative to one another. By pressure or tension on the clamping element, the fixing of the layers is canceled and the spring tensioned. When the clamping element is under no pressure or tension, it returns to its starting position on account of the spring mechanism and fixes all the layers relative to one another. This embodiment of the clamping element has the advantage that the clamping element can be operated with just one finger, for example.

The described functions of the fixing element are controllable and repeatable, such that great flexibility of the fixing element is ensured. In particular, the fixing element is also intended to ensure that the puncture system can be adapted to individual living beings and their individual anatomy and to the anatomy of different body regions. The suspected subcutaneous depth of the structure that is to be punctured can be taken into account even before the start of the puncturing procedure, since the pointed part of the puncture needle protruding from the inner tubular body can be limited in terms of its free length toward the living being in which the puncture is to be performed. This also reduces the danger of deeper anatomical structures being accidentally punctured, in particular by an inexperienced user. This represents an important safety aspect of the new puncture system.

In an advantageous development, the sealing element is fixed on the outside and/or inside of the inner tubular body. It is moreover advantageous if the sealing element is designed as a plastic coating of the inner tubular body, in particular as a PTFE coating. This has the advantage that an exchange of fluid between the inner tubular body and the outer tubular body is effectively and efficiently suppressed by simple design means.

In an advantageous development, the inner tubular body has an uneven surface on the outside. An uneven surface can be formed, for example, by the inner tubular body being made from a spirally wound material, for example as in a spiral spring, as a result of which an uneven surface is generated. The flexibility of the inner tubular body can be increased by such a winding, thus permitting easier application to the patient. The material can also preferably be easily discernible by ultrasound and X-ray. In the case of an uneven surface, it may be advantageous if the latter, at least in a subregion of the end near the patient, is covered by the sealing element, in particular covered in an airtight manner. When producing an inner tubular body with an uneven surface, it can happen that the inner tubular body is permeable to fluid in relation to the outer tubular body, particularly in the case of a spiral winding. By means of the sealing element, an exchange of fluid between the inner tubular body and the outer tubular body can be easily prevented at least in a subregion of the patient-near end of the puncture system.

It is also possible that a tubular hollow body for application to a living being is made at least partially of a metal, wherein the tubular hollow body has an uneven surface and, on the outside or on the inside, is provided at least partially with a sealing coating, without being integrated in a special puncture system. It is moreover advantageous if the tubular hollow body has a spiral structure. By means of the spiral structure, the tubular hollow body has great flexibility, which permits easier application to the patient. An at least partial sealing of the tubular hollow body by the coating ensures that the flexibility is maintained and at the same time that the tubular hollow body is impermeable to fluid, thus permitting, for example, removal of body fluids or administration of medication through the tubular hollow body.

If necessary, the tubular hollow body can additionally be strengthened with further structures or elements, e.g. by transverse, longitudinal or diagonal structures or elements, which can also comprise or span a certain distance of the tubular hollow body and thereby counteract an unwinding of the tubular hollow body.

The tubular hollow body can be sealed, for example, by a plastic coating, for example a PTFE coating, on the inside and/or outside of the tubular hollow body. The tubular hollow body can be made of a metal, for example stainless steel. Thus, an electrical conductivity of the tubular hollow body can also be achieved, such that an ECG signal, for example, can be detected to permit monitoring of the position in the body.

A tubular hollow body can be wound, for example, like a spiral spring from a metal. The individual layers can lie closely on one another such that they are in contact with one another. This is similar to the construction of the already known Seldinger wire, which is made from a tightly wound steel wire. By virtue of the tightly wound layers of metal, the tubular hollow body is resistant to cutting and piercing. A sealing coating on the outside and/or inside of the tubular hollow body renders the tubular hollow body impermeable to fluid. Thus, for example, it cannot draw in air during aspiration. Advantageously, the tip of the tubular hollow body is able to bend back at the end near the patient, so as to avoid injury to the punctured body part.

However, it is also conceivable that the tubular hollow body has grooves distributed about the circumference, for example like a corrugated pipe, which grooves provide an uneven surface, and a high degree of flexibility of the tubular hollow body is thus achieved. The grooves run continuously about the full circumference of the tubular hollow body and are advantageously distributed in parallel at equal or unequal intervals along the length of the tubular hollow body. The tubular hollow body thus has a changing diameter. In this way, it is possible that the tubular body can be oriented in different positions. However, it is also conceivable that the grooves can extend in a spiral formation distributed about the circumference. Such spiral grooves have the advantage that the pressure loss of a fluid conveyed through the tubular hollow body is reduced and, at the same time, a swirling movement of the fluid can be achieved.

A tubular hollow body of this kind can be used in different medical fields. For example, it can be used as a breathing tube. In principle, it can be used whenever two or more fluid-filled spaces are to be connected so as to communicate with each other, in which case one or more spaces thereof can be located in a living being and one or more spaces can be located, for example, in a technical apparatus. However, a use for pleural puncture, bladder puncture, tracheal puncture or abscess puncture is also conceivable, with or without subsequent catheterization. It can in principle be used for puncturing and/or catheterization in all body cavities and spaces within the body. This is permitted in particular by the correct position determination of the tubular hollow body, since aspiration of the suspected content of the structure to be punctured can be possible at any time. If the tubular hollow body lies in a punctured body part, position determination can be carried out at any time on the basis that the tubular hollow body communicates both with the content of the structure to be punctured and with the aspiration means, for example by gas exchange or via a liquid column.

A new kind of puncturing principle is obtained in that a position determination of the kind just described can take place as often as necessary if the puncture system has not yet reached its final position or if an optimal final position of the puncture system is still being sought by the user.

The tubular hollow body can be used here independently of a puncture system. Thus, although it can be used in combination with a puncture system, this is not a precondition for application to the patient. For example, the tubular hollow body can be used as an inner tubular body of the above-described puncture system in order to achieve great flexibility of the inner tubular body and thus facilitate application to the patient. A patient can be understood as meaning both human and animal living beings.

In an advantageous development, the puncture system can have at least one fastening element, wherein the fastening element is designed to fix the puncture system to a patient. It is thus possible to ensure safe use of the puncture system during ongoing operation. The fixing of the puncture system can be done, for example, by suturing it to the skin. However, a click/clip mechanism is also conceivable for fixing the puncture system to the skin. By means of a click/clip mechanism, fine skin staples or the fastening element are pressed in the direction of the skin, such that the skin staples penetrate the skin or the connective tissue and ensure that the puncture system is securely fixed. However, the puncture system can be released at any time, since the skin staples can be easily pulled out of the patient. It is thus possible to omit time-consuming suturing of the puncture system. Moreover, the just described procedure with the click/clip mechanism can be repeated as often as necessary. Thus, if it is inserted too deep into the body, the puncture system can be drawn back by a certain distance in order to correct its position. In this way, repeated suturing is no longer required.

It is also conceivable that the puncture system has liquid-filled elements which can be designed, for example, as gel pads and contain an adhesive liquid or a gel. The gel pads tear open on contact, whereupon the adhesive liquid or the gel escapes from the gel pads, and the puncture system is fixed to the patient by the adhesive liquid or the gel.

The puncture system can have a holding body that makes it easier for the user to hold the puncture system. Such a holding body improves the handling of the puncture system by the user, such that easier application to the patient can be achieved. It is also advantageous if the holding body has a recess, wherein the recess is designed for guiding a thread. In this case, a pull can be exerted by a suture in the direction of the patient, such that the fixing of the puncture system can be improved. A second holding body can be arranged at the end near the patient. This holding body can be designed such that it can be arranged fixed in position, but displaceably relative to the outermost layer of the puncture system. In this way, the puncture system can be operated safely with two hands.

According to an advantageous development, the puncture system has a mandrel for stabilizing the inner tubular body, the outer tubular body and/or the puncture needle. A mandrel serves as an aid for insertion of the tubular body and/or of the puncture needle into the punctured body part. The mandrel can be removed after at least one layer of the puncture system has been positioned. Moreover, the mandrel can be pulled back a distance if necessary. A mandrel can be designed, for example, as a hollow cannula, wherein the mandrel stabilizes and thus facilitates the guiding of the individual layers.

Moreover, a mandrel can prevent the puncture needle from removing or punching out a cylinder of skin which, during the further course of the insertion procedure, can pass deeper into the body. This opens up new areas of use for the puncture system, for example uses near the spinal cord and near the nerves in general. It may be advantageous here if the mandrel is not hollow but solid. The mandrel then fills the lumen of a tubular body completely, so as not to punch out any tissue cylinder.

The puncture needle can accommodate a mandrel which can be adjusted in position by the fixing element, and fixed in said position, or which can remain unaffected by the function of the fixing element.

It is advantageous if the inner tubular body is made at least partially of a metal or is coated with a metal. It is thus possible to prevent the puncture needle from accidentally piercing the inner tubular body.

It is advantageous if, after a body part has been punctured by means of a puncture portion of the puncture needle protruding from a patient-near end of the puncture system, the inner tubular body can be pushed at least partially out of the patient-near end of the puncture system from the outer tubular body and is designed such that at least part of the puncture portion of the puncture needle protruding from the patient-near end of the puncture system is received in the puncture lumen of the inner tubular body. This has the advantage that the outer tubular body can be applied much more easily and more quickly to the patient. By means of the multi-layer structure, it is possible, after the puncture has been performed, that the inner tubular body can be pushed over the puncture needle into the opening thus formed. The inner tubular body already protects the punctured vessel against damage caused by the tip of the puncture needle. The inner tubular body functions as an aid for inserting the outer tubular body, since the outer tubular body can be pushed over the inner tubular body to the desired position.

However, the inner tubular body can also be left in its position when the puncture system is located in the final position. This may also be expedient in particular when further structures located inside the body, for example small blood vessels, are to be selectively reached by the patient-near opening of the inner tubular body. A radiopaque embodiment of the inner tubular body means that the position of the latter can additionally be verified. Moreover, contrast agent for example can be injected through the inner tubular body. The properties mentioned can also in particular open up areas of use in interventional medicine.

At the end distant from the patient, the puncture system can have an aspiration aid or an aspiration port for the attachment of an aspiration aid. The aspiration aid, which can be designed as a conventional syringe for example, can be connected via the aspiration port to the puncture needle, for example. However, it is also conceivable that the aspiration aid can be connected to the inner or outer tubular body. In this way, aspiration can be used at any time to check whether the patient-near region of the puncture system is still located in the target structure. By aspiration of blood, for example, it is thus possible to verify whether the patient-near region of the puncture system is still located in a blood vessel.

An underpressure element can be arranged on the puncture system, wherein the underpressure chamber fills automatically with liquid or blood after the puncture has been performed. The position of the puncture system can be easily determined in this way, since the puncture system is located either in a venous or an arterial vessel depending on the color of the blood. The underpressure element can be attached, for example, instead of an aspiration means. Alternatively, an underpressure element can also be attached to a branch or a three-way valve of the puncture system. Alternatively or in addition, it is also possible for several underpressure elements to be attached in the ways just described. They can be easily put in place and also easily removed again.

The puncture system can have an inflatable cuff which is arranged, for example, on the outside of the outer tubular body. Such a cuff can seal off the puncture system from the outside, by means of the cuff, introduced under the skin, being inflated or filled with liquid, and the puncture system is thus sealed off from the outside. In addition, the puncture system can thus also be stabilized in its position, in particular in hollow bodies such as the trachea.

The puncture system can have an interposed Y-piece at the patient-distant end, wherein three-way valves can be mounted on the Y-piece. The three-way valves can in this case be attached to an extension of the Y-piece. However, it is also conceivable that the three-way valves can be attached directly to the Y-piece. This could be effected, for example, by a latch element on the Y-piece, by means of a three-way valve being able to be plugged into a latch element. The Y-piece can be mounted so as to be rotatable about its longitudinal axis, such that the Y-piece can be rotated to an advantageous position by the user. A separate mounting of the three-way valves is also possible, such that a very high degree of flexibility is ensured and the user is allowed optimum control. The three-way valves can in this case, for example be mounted so as to be rotatable about their own axis. Advantageously, filters can also be integrated in the three-way valves, which filters are able, for example, to prevent entry of air, particles or bacteria into the body of a living being. Alternatively, however, filters of this kind can also be integrated at other positions of the puncture system.

The puncture system can be of a modular configuration, such that parts of the puncture system can be removed when not needed. For example, the Y-piece can be detached when no division of the catheter hose is necessary, for example no division into several lumens, work channels or flow channels. This could be done via a screw connection, for example. The Y-piece can in this case be designed as a detachable cover plate.

The puncture system can advantageously be at least partially transparent, in order to permit detection and identification of fluids in the puncture system. The direction of flow of the fluid can also be determined in this way.

Another particular aspect of the catheter according to the invention is that it is possible to use an inner tubular body with a small lumen. This has the advantage that the skin opening created by the puncture needle does not have to be appreciably widened when the inner tubular body is pushed through. In particular, no dilation in the usual medical sense is required here. Therefore, the catheter according to the invention can also be embodied without a dilation cannula. Instead, the inner tubular body has the function of securing the lumen created by the puncture needle. The inner tubular body can therefore also be designated as a lumen-securing cannula. According to an advantageous development of the invention, the external diameter of the inner tubular body is therefore at most twice as great as the external diameter of the puncture needle. In an advantageous development, the external diameter of the inner tubular body is at most 1.5 times as great as the external diameter of the puncture needle. The diameters here can be made specific to the particular use. For example, it is conceivable for the puncture system to be made available in large diameters and also smaller diameters.

In contrast to other known proposals, a puncture needle is thus proposed which has a smaller diameter than the catheter hose and which thus only leaves behind a small hole in the skin.

Herein also lies an important advantage over known catheter solutions. In known systems, for example, use is made of a cannula which has a large diameter and through which the catheter hose is then inserted into the vein. The cannula can be left in place or, if appropriate, severed and removed. In such systems, the puncture hole in the skin has a larger diameter than the catheter hose, which generally leads to bleeding from the site of entry of the catheter hose into the skin. Moreover, the diameter of the catheter hose to be inserted is limited by the diameter of the cannula. Since the latter already has to have a certain diameter, the diameter of the catheter hose is limited, and it is therefore not possible to infuse particularly large amounts of liquid per unit of time into the vein. A further disadvantage of known systems is that the puncture needle used for the puncturing has an equally large diameter, such that the puncture causes trauma. Inaccurate punctures can result in considerable injuries. Such disadvantages are overcome by the present invention.

Accordingly, only a slight change of caliber is present at the transition from the puncture needle to the inner tubular body. To further simplify the insertion of the inner tubular body, it can be rounded at the end near the patient.

Compared to the inner tubular body, the outer tubular body has a greater change of caliber, which is required also to provide a necessary internal diameter needed for delivery of liquids in large amounts. According to an advantageous development of the invention, the external diameter of the outer tubular body is therefore at least twice as great as the external diameter of the inner tubular body. In this way, large flow rates are ensured. According to an advantageous development of the invention, the external diameter of the inner tubular body is at least three times as great as the external diameter of the inner tubular body.

Accordingly, a dilation step is required only when inserting the outer tubular body into the vein.

The puncture system can have a sterile sleeve, wherein the sterile sleeve can lie as a fourth layer over the outer tubular body or the puncture system. The puncture system can be additionally stabilized by such a sterile sleeve.

The sterile sleeve, particularly a sleeve directed toward the patient-near end, can be made of more solid material. In this way, although the sleeve is held back on the skin during the advance of the puncture system, in particular of the outer tubular body, it additionally stabilizes the puncture system, particularly if the outer tubular body is located outside the body. Since the sterile sleeve cannot pass the skin, a puncture system is obtained which has somewhat more solid properties outside the body and somewhat more flexible properties inside the body.

Elements like suction cups would also be conceivable which, at the start of application, can be placed with a stabilizing effect onto the skin and thus prevent slipping of the puncture system. However, a stamp-like attachment is also possible which can be placed with a stabilizing effect onto the skin prior to application. A bead-like widening or some other kind of widening of the patient-near end of the sterile sleeve is for example possible, for example in the form of a protective ring, which can also be mounted separately. Alternatively, the widening can also be configured like a cap, a projection or a flap.

At least one slide element can be arranged between the sterile sleeve and the outer tubular body, as a result of which an optimal longitudinal displaceability of the two layers is ensured. The slide element can be designed, for example, as a ball or as a surface with ball-like subelements, wherein the ball decreases the frictional resistance of the outer tubular body relative to the sterile sleeve.

Alternatively or in addition, a lubricant gel or another liquid or solution can moreover be arranged between the outer tubular body and the sterile sleeve. Alternatively or in addition, surface coatings can be used which decrease the traditional resistance between the sterile sleeve and the outer tubular body. Alternatively or in addition, a space empty of air, in the sense of a vacuum, can be generated and maintained by tight closure. Alternatively or in addition, nanotechnologies can be used.

With a sterile sleeve of this kind, a closed system can be created that satisfies hygiene aspects. Moreover, an extremely robust puncture system is obtained which is also suitable for puncturing under unfavorable conditions and in special situations. Alternatively or in addition, the sterile sleeve can also be tubular or lamella-shaped. As the puncture system is passed through the skin, the sterile sleeve is shortened in a manner similar to a telescope, by means of different fine layers of the sterile sleeve overlapping each other and thereby shortening the sterile sleeve. Alternatively or in addition, the sterile sleeve can also be separable or tearable and thus removable when the puncture system is located in the final position and no sterile sleeve is therefore needed any longer. The sterile sleeve can advantageously be transparent, such that the advance of the outer tubular body through the skin of the patient can be precisely tracked at all times. The sterile sleeve is advantageously resistant to cutting and piercing.

The invention can advantageously be refined with the following features:

The inner tubular body can be insertable laterally into the puncture system, in which case, for example, a connection element can permit a connection into the lumen of the outer tubular body. The inner tubular body can in this case for example, already be located in an additional sterile sleeve prior to insertion.

A displaceability of the individual layers can be effected, for example, with the aid of a rotary wheel, by means of the rotary wheel interacting with the layer to be displaced in such a way that, by rotation of the rotary wheel, one of the layers can be moved forward and/or backward.

The puncture needle is arranged in the inner tubular body in such a way that, after the puncture has been made, the puncture needle can be moved back into the inner tubular body by the inflowing fluid.

The individual layers can be reinforced specifically in the region of fixing by the fixing element, in particular through a choice of material suitable for avoiding damage to the puncture system in the region of the fixing.

The outer tubular body can have recesses for the entry or exit of liquid. The recesses can be positioned in this case at the patient-near end of the outer tubular body. Several outlet holes can be arranged in order to increase the flow rate of the liquid that is to be infused. The shape of the recesses is variable, such that the direction of flow can be favorably influenced. Thus, the recesses can in particular be slit-shaped or beveled.

The recesses can have retaining elements which permit a flow of liquids only in a defined direction. This may be advantageous, for example, in dialysis catheters in which a liquid is in each case allowed to pass only in one direction through a dedicated channel.

The puncture system can have a safety element, wherein the safety element passes over the puncture needle after removal of the puncture system, such that the patient or user cannot suffer needlestick injuries. A pulling mechanism would also be conceivable as a safety element, in which case safety is afforded by the puncture needle being turned back.

Application of the puncture system is possible in many fields of use. For example, a color scheme and/or numerical scheme can make the application process clearer and thus considerably enhance the safety of the patient.

The puncture system can have both hydrophobic and hydrophilic components, wherein components near the user can, for example, be designed to be hydrophobic, such that liquids are repelled and thus cause less contamination of the puncture system. This can be done, for example, in the course of a corresponding surface coating of the individual layers. Moreover, it has the advantage that the insertion of the individual layers into a body part can be made easier and/or the flow ratios within the tubular body can be influenced.

The outer tubular body can be designed to be resistant to cutting and piercing. This can be achieved, for example, by a cover or by the use of a suitable material. However, it is also conceivable that all the layers of the puncture system are designed to be resistant to cutting and piercing.

The puncture system can have a detector element, in which case the detector element has a pressure-sensitive design and, in the event of an increased pressure, the detector element fills with the liquid. In this way, an arterial puncture can be detected, since the pressure in the arterial system is in principle greater than in the venous system. The detector element can be designed here as a pressure-sensitive switch or pressure-sensitive valve by which two mutually separate indicator chambers are filled with blood depending on the prevailing pressure conditions, for example in the blood circulation of a living being. In this way, a differentiation can be made between a venous puncture and an arterial puncture. The inflow to the "arterial chamber" opens only when a certain pressure is exceeded. When this chamber fills with blood, it is possible to infer an erroneous arterial puncture, if a venous puncture is sought. This additionally increases patient safety. The pressure sensitivity can be variable in this case and, for example, can be adapted to the circulatory situation or the clinical situation of the patient.

The puncture system can have check valves which prevent a reverse outward flow of liquids and the penetration of air into the puncture system and thus into the patient's body.

The outer tubular body can have a valve or a valve mechanism which is designed in such a way that, when the inner tubular body is removed, there is an automatic closure of the work lumen of the outer tubular body receiving the inner tubular body.

The puncture system can be coated with a material at various locations that can come into contact with blood, wherein the material, by means of a color change, indicates the oxygen content of the blood or the oxygen partial pressure of the blood.

The puncture system can have an antibacterial or antimicrobial coating.

The puncture system can be provided, at at least one location, with a special surface coating which indicates contamination, e.g. with bacteria. This surface material can also have fluorescent properties.

Alternatively, a spray is also conceivable which, after being sprayed on, can make contamination visible.

To read off the values of the oxygen content, for example, a color chart can be used which can also be printed directly on the puncture system or on the packaging of the puncture system.

The puncture system can be adjustable in length in order to achieve individual adaptation to different patients. For example, the puncture system can have at least in part an accordion configuration in order to achieve longitudinal displaceability.

In a puncture system of the kind described above, a conventional Seldinger wire can be used, by virtue of the latter being able to be introduced into the patient through the puncture needle or the inner or outer tubular body.

In the event of accidental kinking of the puncture system, it can be advantageous if the aspiration means is designed with a blocking action, such that suctioning or delivery of liquids is no longer possible.

One or more components of the puncture system can be shapeable or deformable, in particular by active external influences. In this way, individual adaptation to the respective patient is possible, for example to the individual size of the patient. Moreover, adaptation to the particular anatomical circumstances is also possible, for example to specific courses of blood vessels and specific configurations of cavities and spaces within the body.

One or more components of the puncture system can be of a solid or rigid design. In particular, most or all of the components can also be of a solid or rigid design for use in specific fields, e.g. in the field of minimally invasive surgery. In this way, a puncture system is obtained which has properties similar to those of a trocar and which in its final position, after removal of one or more layers, like the inner tubular body, can provide access for surgical or endoscopic instruments, for example, into a cavity or space within the body.

The invention is explained in more detail below on the basis of illustrative embodiments, with use being made of the drawings, in which.

Figure 1:
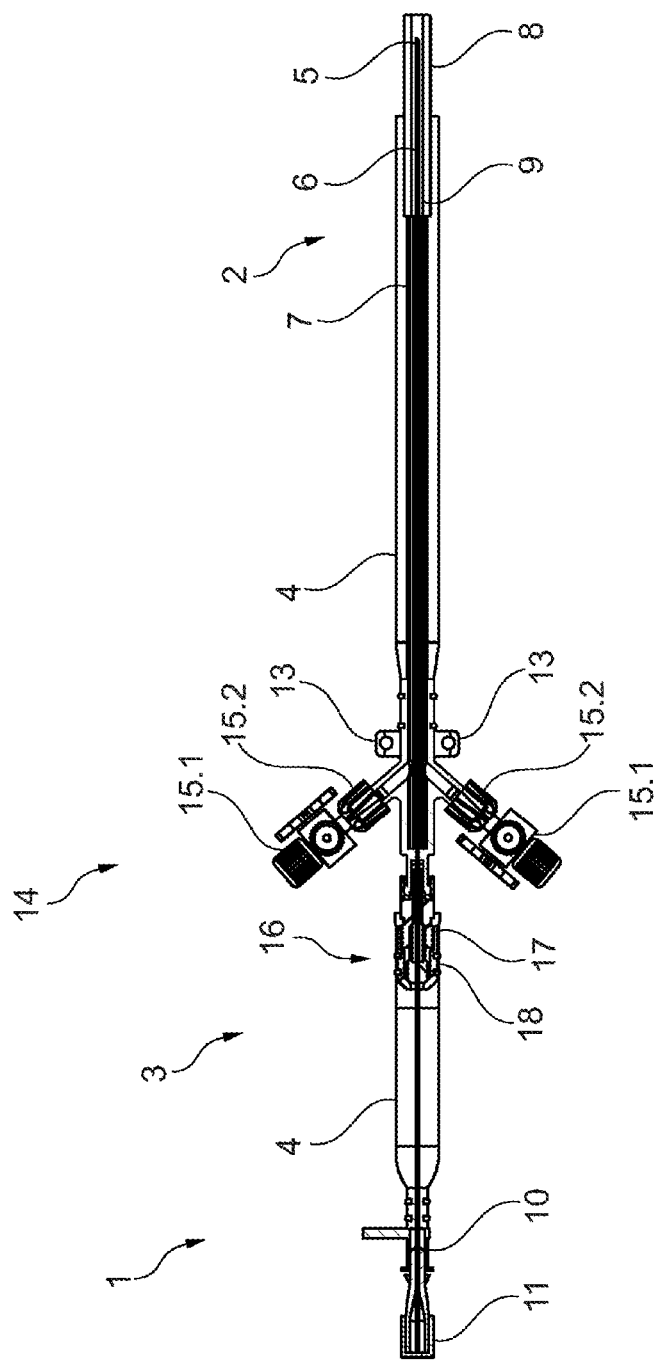
FIG. 1 shows a puncture system in a sectional view.

FIG. 1 shows a puncture system 1 in a sectional view. All the lumens of the puncture system 1 can be filled with sterile saline or distilled water in the state when supplied, so that the puncture system 1 can be used directly with venting.

The puncture system 1 has a patient-near end 2, wherein the patient-near end is designed to be inserted into a patient, for example into a vein. A patient-distant end 3 is arranged directed away from the patient, wherein the puncture system 1 is operated by a user via the patient-distant end 3. It is clear that the puncture system 1 has an outer sleeve 4, in particular a sterile sleeve 4, wherein a puncture needle 5, an inner tubular body 6 and an outer tubular body 7 are arranged inside the sterile sleeve. The puncture needle 5 is guided longitudinally displaceably inside the work lumen of the inner tubular body 6, wherein the inner tubular body 6 is guided longitudinally displaceably in the work lumen of the outer tubular body 7.

FIG. 1 shows the puncture system 1 in a delivery state. In the delivery state, the puncture needle 5 does not yet protrude from the puncture system 1 at the patient-near end 2. The puncture needle 5 is still provided with a protective cap 8, which has to be removed prior to application of the puncture needle to a patient. A protective cap 8 of this kind prevents a situation in which the puncture needle 5 injures the user and/or the patient even before the application and in which the puncture needle is exposed to non-sterile influences.

Applying the puncture system 1 to a patient can be done, for example, by performing the following steps, which can be illustrated on the puncture system 1 by suitable color coding or numbering:

1. Puncturing a vein with the puncture needle 5
2. Advancing the inner tubular body 6 into the vein to the desired position
3. Removing/pulling back the puncture needle 5
4. Closing the inner tubular body 6

5. Advancing the outer tubular body 7 over the inner tubular body 6 into the vein
6. Removing/pulling back the inner tubular body 6

The outer tubular body 7 has a dilation body 9, wherein the dilation body 9 permits step-by-step widening of the punctured site, such that the outer tubular body 7, by virtue of having a greater diameter than the inner tubular body 6, can be inserted into the punctured body part. The dilation body 9 tapers here at an angle of less than 11 degrees, preferably less than 10.5°, thus ensuring reliable widening of the punctured site.

It is clear that the sterile sleeve 4 has a stabilizing effect on the puncture system 1. The sterile sleeve 4, on account of its size, cannot pass through the punctured site. Thus, the sterile sleeve 4 can be formed for example from a solid material, wherein the puncture system 1 with the inner tubular body 6 and the outer tubular body 7 inside the body of a patient has flexible properties and, by means of the outer sleeve 4 outside the body, has a stabilizing effect on the puncture system 1, such that application to the patient is made easier. The sleeve 4 is transparent, such that the longitudinal displacement of the puncture needle 5, of the inner tubular body 6 and of the outer tubular body 7 is discernible to the user at all times. The puncture needle 5, the inner tubular body 6 and the outer tubular body 7 can be transparent.

An attachment body 10 for attaching a syringe is provided at the patient-distant end 3, wherein the syringe can be used, for example, to perform aspiration of blood. A mandrel 11 on the attachment body 10 facilitates the insertion of the outer tubular body 7 and inner tubular body 6 and of the puncture needle 5.

The puncture system 1 moreover has two fastening elements 13, wherein the fastening elements 13 are designed to fix the puncture system 1 to the patient. For this purpose, the puncture system 1 can be sutured to the patient, for example, at the fastening elements 13.

A Y-piece 14 is arranged on the puncture system 1 between the patient-near end 2 and the patient-distant end 3. Three-way valves 15.1 are attached to the Y-piece 14. It is thus easily possible to provide several access routes to the puncture system, which for example permit simultaneous administration of different liquids. The three-way valves 15.1 are connected here to the Y-piece 14 via a latch mechanism 15.2, which permits rapid and reliable connection by latching the three-way valves 15.1 in the latch mechanisms 15.2. For example, syringes, infusion lines or an electrical connection line for a continuous ECG capture via the puncture system 1 can be attached via the three-way valves 15.1. Advantageously, filters can also be integrated in the three-way valves, which filters can, for example, prevent entry of air into the human body. Flaps that allow liquids to flow only in a defined direction can be integrated in the three-way valves. An unintended flow of liquid from the puncture system in the direction of the user can thus be prevented.

The puncture system 1 has a fixing element 16, wherein the fixing element 16 is formed of a longitudinally slotted sleeve 17 and a union nut 18. It is clear that the longitudinal displaceability of the puncture needle 5, of the inner tubular body 6 and/or of the outer tubular body 7 can be reduced or canceled by the fixing element 16. By tightening the union nut 18, it is possible for the puncture needle 5, the inner tubular body 6 and/or the outer tubular body 7 to be secured relative to each other in such a way that the puncture system 1 is stabilized in its position, and application to the patient is thus made easier. It is also conceivable, for example, for only two of the three layers to be able to be fixed longitudinally displaceably relative to each other, such that other layers can be fixed depending on the application step.

Figure 2:
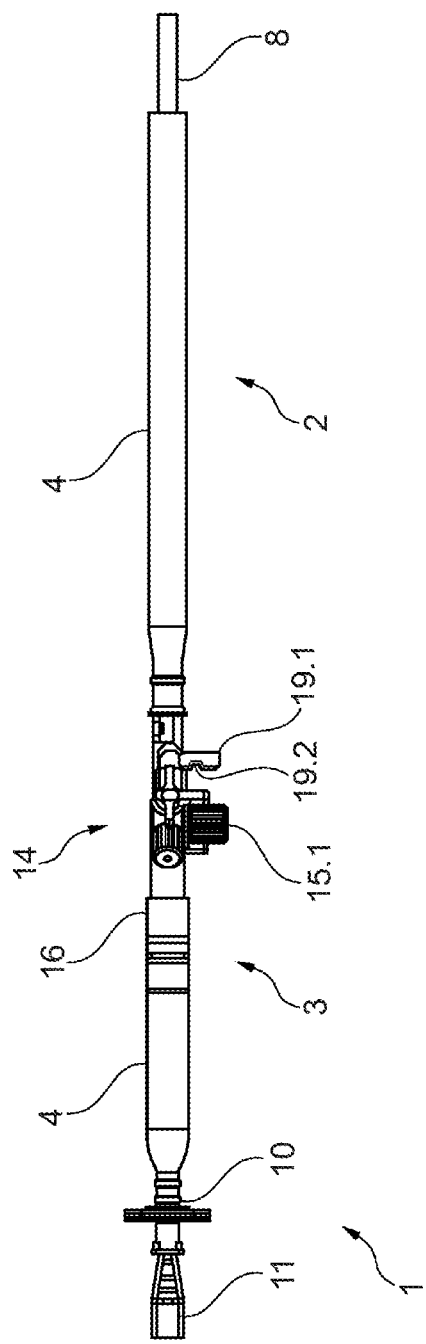
FIG. 2 shows a puncture system according to FIG. 1 in a side view, in a position rotated through 90°.

FIG. 2 shows a side view of a puncture system 1 according to FIG. 1, in a position rotated through 90°. It can be seen from this view that the puncture system 1 has a holding body 19.1, wherein the holding body 19.1 makes using the puncture system 1 easier for the operator, since it allows the user to use his second hand to hold and control, or further stabilize, the patient-near end 2 during the application process.

The holding body has a recess 19.2, which is configured for guiding a thread. By way of a suture sutured to the patient via the recess 19.2 and the fastening elements 13 (see FIG. 1), a tensile force can be applied in the direction of the patient, such that the fixing to the patient is improved.

Figure 3:
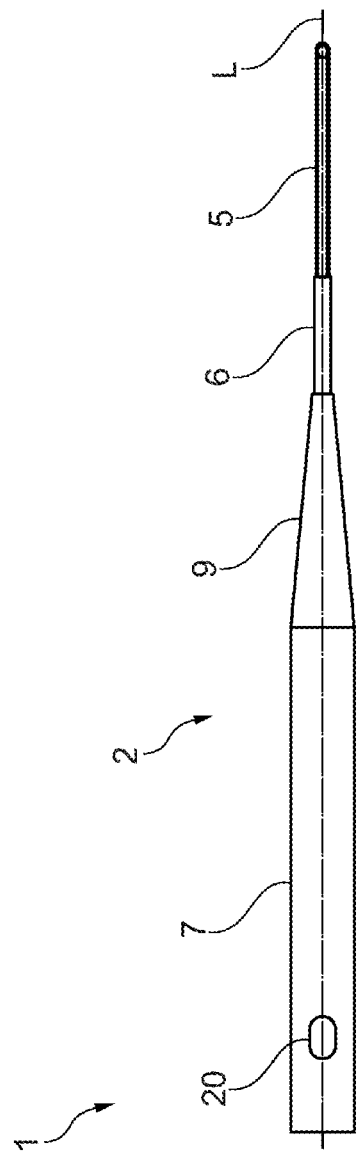
FIG. 3 shows an enlarged illustration of the patient-near end of the puncture system, in a side view.

FIG. 3 shows an enlarged illustration of the patient-near end 2 of the puncture system 1. The three-layer structure of the puncture system 2 can be clearly seen. The puncture needle 5 is arranged inside a work lumen of the inner tubular body 6, longitudinally displaceable in the direction of the longitudinal axis L, and the inner tubular body 6 is arranged in a work lumen of the outer tubular body 7. It is also clear that the outer tubular body 7 has a dilation element 9, wherein the dilation element 9 tapers at an acute angle of less than 11°, such that a widening of the punctured body part can be achieved, with the result that the outer tubular body 7 can be guided through the punctured site into the body of the patient. By contrast, a dilation body on the inner tubular body 6 is not necessary, since the difference in diameter to the puncture needle 5 is so small that the inner tubular body 6 can be inserted without any problem through the punctured site and into the body.

It will also be seen that the outer tubular body 7 has a hole 20. Such a hole 20 on the outside of the outer tubular body 7 can serve as a liquid outlet. The hole 20 is not limited here in terms of its shape, and indeed it can also be configured differently. Alternatively, the holes can have a beveled or slot-shaped design, for example, in order to favorably influence the direction of flow of liquids.

Figure 4:
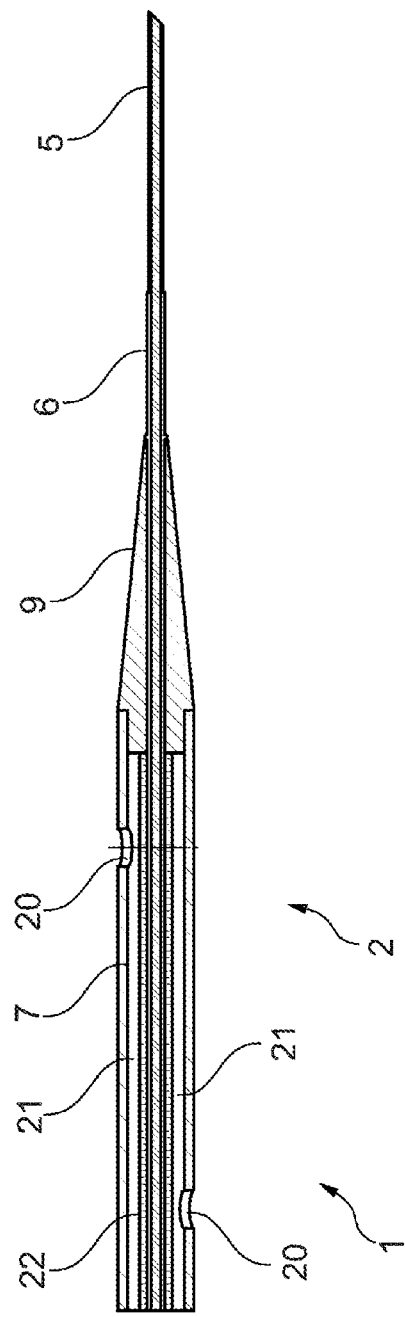
FIG. 4 shows an enlarged illustration of the patient-near end of the puncture system according to FIG. 3, in a sectional view.

FIG. 4 moreover shows an enlarged illustration of the patient-near end 2 of the puncture system 1 according to FIG. 3, in a sectional view. It will be seen that the puncture system 1 has a plurality of holes 20 on the outside of the outer tubular body 7, wherein the holes 20 are arranged at different positions at the patient-near end 2.

A respective channel 21 of the outer tubular body is assigned to each of the holes 20. This can be advantageous in particular if liquids are intended to be able to enter and also leave. This can then take place via one of the autonomous channels 21.

It will also be seen from FIG. 4 that the inner tubular body 6 has a sealing element 22 extending about the circumference. The sealing element 22 can be a PTFE coating, for example, and can be applied to the outside of the inner tubular body 6. If, for example, the inner tubular body 6 has a winding structure, sealing is necessary in order to ensure that no flow of fluid can take place between the inner tubular body 6 and the outer tubular body 7. In FIG. 4, the sealing element 22 extends only partially about the tubular body 6. However, it is also conceivable that the sealing element 22 can extend about the entire circumference of the tubular body 6.

Figure 5:
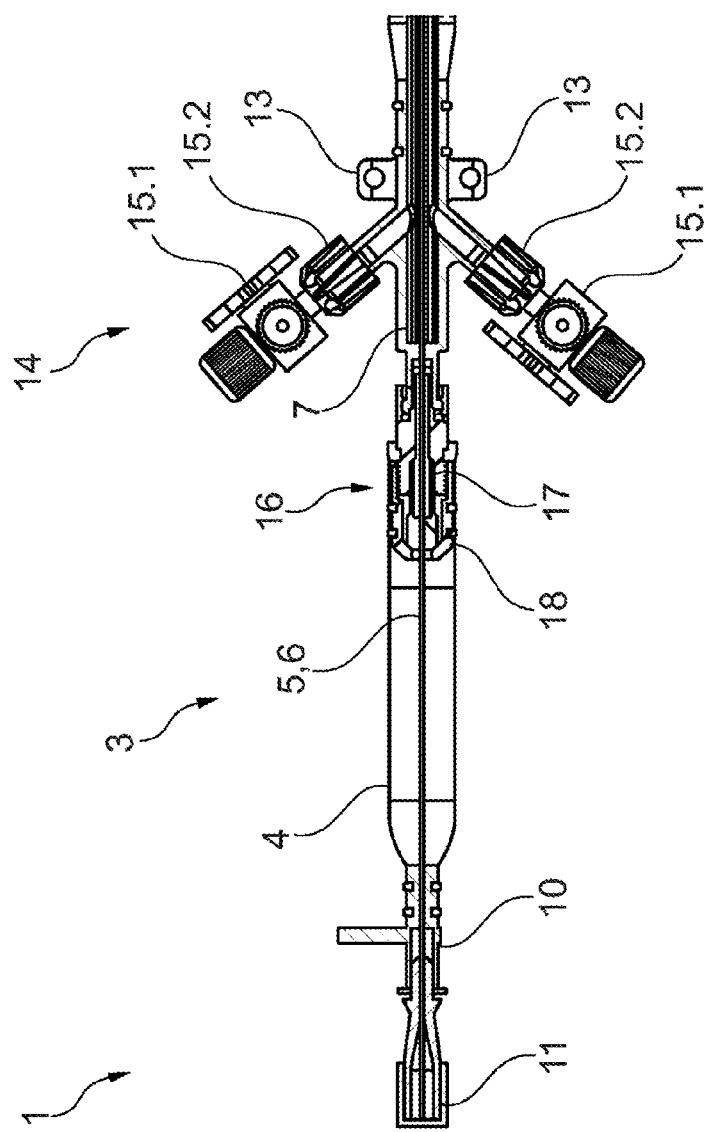
FIG. 5 shows an enlarged illustration of the patient-distant end of the puncture system according to FIG. 1, in a sectional view.

FIG. 5 shows an enlarged illustration of the patient-distant end 3 of the puncture system 1 according to FIG. 1, in a sectional view. The fixing element 16 is formed of a longitudinally slotted sleeve 17 and a union nut 18. It is clear that, after the union nut 18 has been tightened, the puncture needle 5 and the inner tubular body 6 are pressed into the longitudinally slotted sleeve 17 and the longitudinal displaceability is in this way reduced. The matter of in which layers the longitudinal displaceability is reduced is not limited to this illustrative embodiment. It would also be conceivable for the outer tubular body 7 to be received in the longitudinally slotted sleeve 17, such that the longitudinal displaceability of all three layers can be reduced or canceled.

FIGS. 1 to 5 are to be understood as possible illustrative embodiments. Other forms of the teaching according to the invention are also conceivable. Moreover, the configurations of the illustrative embodiments are not inextricably linked with one another, and therefore, for example, the implementation of the invention is not dependent on the specifically described configurations of the illustrative embodiments. For example, it is always conceivable to vary the number, length or size of the individual elements.

The invention claimed is:

1. A puncture system, comprising:
   an outer tubular body which is designed to remain in a body part of a living being,
   at least one inner tubular body, and
   a puncture needle,
   wherein the inner tubular body is guided through a work lumen of the outer tubular body and is longitudinally displaceable relative to the outer tubular body,
   wherein the puncture needle is guided through a puncture lumen of the inner tubular body, and
   wherein the inner tubular body is longitudinally displaceable relative to the puncture needle,
   wherein the puncture system has one, more or all of the following features a), b), c):
   a) the puncture system has a manually actuatable fixing element moveable by manual actuation at least into a fixing position and into a release position, wherein, in the fixing position, the longitudinal displaceability
      a1) of the inner tubular body relative to the outer tubular body and/or
      a2) of the puncture needle relative to the inner tubular body and/or
      a3) of the puncture needle relative to the outer tubular body is canceled or reduced,
      wherein the fixing element is moveable by manual actuation into different fixing positions in which the longitudinal displaceability is in each case adjustable in respect of different combinations of the features a1), a2), and a3),
   b) the puncture system has a sealing element by which the inner tubular body is sealed off relative to the outer tubular body at least at an end positionable near a patient,
   c) the puncture system has, at the end positionable near the patient, a dilation body which serves for inserting the outer tubular body into a body part and through which the inner tubular body is guided, wherein the dilation body tapers at an acute angle of less than 11 degrees.

2. The puncture system as claimed in claim 1, wherein, in the fixing position, the longitudinal displaceability is reduced by the fixing element to an extent that is settable by manual actuation.

3. The puncture system as claimed in claim 1 wherein the fixing element is moveable by manual actuation into different fixing positions in which the longitudinal displaceability is reduced to respectively different extents.

4. The puncture system as claimed in claim 1 wherein the fixing element is designed as a clamping element or has a clamping element, wherein the clamping element performs one or more of
   b1) clamping the inner tubular body relative to the outer tubular body and/or
   b2) clamping the puncture needle relative to the inner tubular body and/or
   b3) clamping the puncture needle relative to the outer tubular body.

5. The puncture system as claimed in claim 1 wherein the sealing element is fixed on the outside of the inner tubular body.

6. The puncture system as claimed in claim 1 wherein the sealing element is designed as a plastic coating of the inner tubular body.

7. The puncture system as claimed in claim 6 wherein the plastic coating is or includes polytetrafluoroethylene (PTFE).

8. The puncture system as claimed in claim 1 further comprising at least one fastening element designed to fix the puncture system to a patient.

9. The puncture system as claimed in claim 1 further comprising a holding body for a user to hold the puncture system.

10. The puncture system as claimed in claim 9, wherein the holding body has a recess designed for guiding a thread.

11. The puncture system as claimed in claim 1 further comprising a mandrel for stabilizing the inner tubular body, the outer tubular body and/or the puncture needle.

12. The puncture system as claimed in claim 1 wherein the inner tubular body is made at least partially of a metal or is coated with a metal.

13. A puncture system, comprising:
    an outer tubular body which is designed to remain in a body part of a living being,
    at least one inner tubular body, and
    a puncture needle,
    wherein the inner tubular body is guided through a work lumen of the outer tubular body and is longitudinally displaceable relative to the outer tubular body,
    wherein the puncture needle is guided through a puncture lumen of the inner tubular body, and
    wherein the inner tubular body is longitudinally displaceable relative to the puncture needle,
    wherein the puncture system has one, more or all of the following features a), b), c):
    a) the puncture system has a manually actuatable fixing element moveable by manual actuation at least into a fixing position and into a release position, wherein, in the fixing position, the longitudinal displaceability
       a1) of the inner tubular body relative to the outer tubular body and/or
       a2) of the puncture needle relative to the inner tubular body and/or
       a3) of the puncture needle relative to the outer tubular body is canceled or reduced,
    b) the puncture system has a sealing element by which the inner tubular body is sealed off relative to the outer tubular body at least at an end positionable near a patient,
    c) the puncture system has, at the end positionable near the patient, a dilation body which serves for inserting the outer tubular body into a body part and through which the inner tubular body is guided, wherein the dilation body tapers at an acute angle of less than 11 degrees, wherein the inner tubular body has an uneven surface on the outside, The puncture system as claimed in claim 8, wherein the uneven surface, at least in a subregion of the end positionable near the patient, is covered by the sealing element.

14. The puncture system as claimed in claim 13 wherein the subregion covered by the sealing element is covered in an air tight manner.

* * * * *